US010060900B2

(12) United States Patent
Kangas

(10) Patent No.: US 10,060,900 B2
(45) Date of Patent: *Aug. 28, 2018

(54) CONCRETE SCREEDING SYSTEM WITH FLOOR QUALITY FEEDBACK/CONTROL

(71) Applicant: SOMERO ENTERPRISES, INC., Fort Myers, FL (US)

(72) Inventor: Matthew A. Kangas, Atlantic Mine, MI (US)

(73) Assignee: SOMERO ENTERPRISES, INC., Fort Myers, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/830,117

(22) Filed: Dec. 4, 2017

(65) Prior Publication Data
US 2018/0088102 A1    Mar. 29, 2018

Related U.S. Application Data

(63) Continuation of application No. 14/697,964, filed on Apr. 28, 2015, now Pat. No. 9,835,610.
(Continued)

(51) Int. Cl.
*E01C 19/00* (2006.01)
*E01C 19/42* (2006.01)
(Continued)

(52) U.S. Cl.
CPC ......... *G01N 33/383* (2013.01); *E01C 19/004* (2013.01); *E01C 19/22* (2013.01);
(Continued)

(58) Field of Classification Search
CPC ..... E01C 19/22; E04F 21/244; G01N 33/383; G01B 11/306; G05B 15/02
See application file for complete search history.

(56) References Cited

U.S. PATENT DOCUMENTS

| 2,796,685 A | 6/1957 | Bensinger |
| 3,604,325 A | 9/1971 | Borges |

(Continued)

FOREIGN PATENT DOCUMENTS

JP    H04179708    6/1992

OTHER PUBLICATIONS

International Search Report and Written Opinion dated Jun. 24, 2015, from corresponding PCT Application No. PCT/US2015/027913, filed Apr. 28, 2015.

*Primary Examiner* — Abigail A Risic
(74) *Attorney, Agent, or Firm* — Honigman Miller Schwartz and Cohn, LLP

(57) ABSTRACT

A method for screeding of an uncured concrete surface includes providing a screeding machine and a control. The uncured concrete surface is screeded and the control processes data captured by the sensors while the screeding machine is screeding the uncured concrete surface. While the screeding machine is screeding the uncured concrete surface, and responsive to data processing by the control of data captured by the sensors while the screeding machine is screeding the uncured concrete surface, the control estimates a flatness or levelness or quality of the surface of the concrete surface being screeded. The control may generate an output indicative of the estimated flatness or levelness or quality of the surface, and/or a display may display information associated with the estimated flatness or levelness or quality of the surface.

27 Claims, 7 Drawing Sheets

Related U.S. Application Data

(60) Provisional application No. 61/985,008, filed on Apr. 28, 2014.

(51) Int. Cl.
*E01C 19/22* (2006.01)
*G05B 15/02* (2006.01)
*G01N 33/38* (2006.01)
*G01B 11/30* (2006.01)

(52) U.S. Cl.
CPC ............ *E01C 19/42* (2013.01); *G01B 11/306* (2013.01); *G05B 15/02* (2013.01)

(56) References Cited

U.S. PATENT DOCUMENTS

| | | |
|---|---|---|
| 3,870,427 A | 3/1975 | Allen |
| RE28,400 E | 4/1975 | Burgin |
| 3,953,145 A | 4/1976 | Teach |
| 4,655,633 A | 4/1987 | Somero et al. |
| 4,759,657 A | 7/1988 | Dorr et al. |
| 4,807,131 A | 2/1989 | Clegg |
| 4,930,935 A | 6/1990 | Quenzi et al. |
| 4,978,246 A | 12/1990 | Quenzi et al. |
| 5,039,249 A | 8/1991 | Hansen et al. |
| 5,129,803 A | 7/1992 | Nomura et al. |
| 5,156,487 A | 10/1992 | Haid |
| 5,258,961 A | 11/1993 | Sehr et al. |
| 5,288,166 A | 2/1994 | Allen et al. |
| 5,288,167 A | 2/1994 | Gaffard et al. |
| 5,328,295 A | 7/1994 | Allen |
| 5,352,063 A | 10/1994 | Allen et al. |
| 5,375,663 A | 12/1994 | Teach |
| 5,549,412 A | 8/1996 | Malone |
| 5,567,075 A | 10/1996 | Allen |
| 5,588,776 A | 12/1996 | Swisher, Jr. et al. |
| 5,752,783 A | 5/1998 | Malone |
| 5,771,978 A | 6/1998 | Davidson et al. |
| 6,027,282 A | 2/2000 | Horn |
| 6,129,481 A | 10/2000 | Tapio et al. |
| 6,152,647 A | 11/2000 | Tapio et al. |
| 6,183,160 B1 | 2/2001 | Tapio et al. |
| 6,227,761 B1 | 5/2001 | Kieranen et al. |
| 6,530,720 B1 | 3/2003 | Green |
| 6,588,976 B2 | 7/2003 | Quenzi et al. |
| 6,623,208 B2 | 9/2003 | Quenzi et al. |
| 6,752,567 B2 | 6/2004 | Miyamoto et al. |
| 6,953,304 B2 | 10/2005 | Quenzi et al. |
| 6,976,805 B2 | 12/2005 | Quenzi et al. |
| 7,044,681 B2 | 5/2006 | Quenzi et al. |
| 7,121,762 B2 | 10/2006 | Quenzi et al. |
| 7,175,363 B2 | 2/2007 | Quenzi et al. |
| 7,320,011 B2 | 1/2008 | Quenzi et al. |
| 7,320,558 B2 | 1/2008 | Quenzi et al. |
| 7,396,186 B2 | 7/2008 | Quenzi et al. |
| 7,491,011 B2 | 2/2009 | Quenzi et al. |
| 7,559,719 B2 | 7/2009 | Nasby |
| 7,677,834 B2 | 3/2010 | Quenzi et al. |
| 7,850,396 B2 | 12/2010 | Pietila et al. |
| 7,891,906 B2 | 2/2011 | Quenzi et al. |
| 7,909,533 B2 | 3/2011 | Quenzi et al. |
| 8,038,365 B2 | 10/2011 | Quenzi et al. |
| 9,835,610 B2 | 12/2017 | Kangas |
| 2001/0048850 A1 | 12/2001 | Quenzi et al. |
| 2004/0071509 A1 | 4/2004 | Frankeny, II |
| 2004/0190991 A1 | 9/2004 | Quenzi et al. |
| 2005/0069385 A1 | 3/2005 | Quenzi et al. |
| 2006/0018715 A1 | 1/2006 | Halonen et al. |
| 2010/0196096 A1 | 8/2010 | Halonen et al. |
| 2012/0263532 A1 | 10/2012 | Rutz et al. |

Screed Pass Details

| Date | Time | Pass # | Canceled Pass # | Row # | Left Pass SPQ | Right Pass SPQ | Flag 1 | Flag 2 | Flag 3 | Flag 4 | Flag 5 | Flag 6 | Flag 7 | Touchdown | Boom Speed | Attitude | Left Fast | Left Slow | Right Fast | Right Slow | Laser | Column Block | Head Rotate | Frame Rotate | Pass Canceled | Pass Duration | Left Data Count | Right Data Count | Left Data Average | Right Data Average |
|---|---|---|---|---|---|---|---|---|---|---|---|---|---|---|---|---|---|---|---|---|---|---|---|---|---|---|---|---|---|---|
| 3/25/2015 | 7:21 AM | 8 | 0 | 1 | 452 | 419 | 0 | 0 | 0 | 0 | 0 | 0 | 0 | 0 | 0 | 0 | 0 | 0 | 0 | 0 | 0 | 0 | 0 | 0 | 0 | 37.1 | 368 | 372 | 0.81 | 0.70 |
| 3/25/2015 | 7:22 AM | 9 | 0 | 1 | 428 | 450 | 0 | 0 | 0 | 0 | 0 | 0 | 0 | 0 | 0 | ▓ | 0 | 0 | 0 | 0 | 0 | 0 | 0 | 0 | 0 | 39.3 | 393 | 390 | 0.64 | 0.70 |
| 3/25/2015 | 7:30 AM | 10 | 0 | 1 | 500 | 500 | 0 | 0 | 0 | 0 | 0 | 0 | 0 | 0 | 0 | 0 | 0 | 0 | 0 | 0 | 0 | 0 | 0 | 0 | 0 | 25.7 | 258 | 258 | 1.05 | 1.16 |
| 3/25/2015 | 7:30 AM | 11 | 0 | 1 | 478 | 485 | 0 | 0 | 0 | 0 | 0 | 0 | 0 | 0 | 0 | 0 | 0 | 0 | 0 | 0 | 0 | 0 | 0 | 0 | 0 | 25.7 | 256 | 258 | 0.72 | 0.80 |
| 3/25/2015 | 7:32 AM | 12 | 0 | 1 | 491 | 500 | 0 | 0 | 0 | 0 | 0 | 0 | 0 | 0 | 0 | 0 | 0 | 0 | 0 | 0 | 0 | 0 | 0 | ▓ | 0 | 42.0 | 419 | 418 | 0.86 | 0.97 |
| 3/25/2015 | 7:41 AM | 13 | 0 | 1 | 477 | 486 | 0 | 0 | 0 | 0 | 0 | 0 | 0 | 0 | 0 | 0 | 0 | 0 | 0 | 0 | 0 | 0 | 0 | ▓ | 0 | 44.8 | 450 | 449 | 0.85 | 0.88 |
| 3/25/2015 | 7:42 AM | 14 | 0 | 1 | 482 | 485 | 0 | 0 | 0 | 0 | 0 | 0 | 0 | 0 | 0 | 0 | ▓ | 0 | ▓ | 0 | 0 | 0 | 0 | 0 | 0 | 36.7 | 364 | 368 | 0.98 | 0.85 |
| 3/25/2015 | 7:46 AM | 15 | 0 | 1 | 482 | 482 | 0 | 0 | 0 | 0 | 0 | 0 | 0 | 0 | 0 | 0 | 0 | 0 | 0 | 0 | 0 | 0 | 0 | 0 | 0 | 11.6 | 111 | 116 | 0.57 | 0.67 |
| 3/25/2015 | 7:47 AM | 16 | 0 | 1 | 495 | 495 | 0 | 0 | 0 | 0 | 0 | 0 | 0 | 0 | 0 | 0 | 0 | 0 | 0 | 0 | 0 | 0 | 0 | ▓ | 0 | 36.2 | 362 | 362 | 0.93 | 0.97 |
| 3/25/2015 | 7:49 AM | 17 | 0 | 1 | 477 | 490 | 0 | 0 | 0 | 0 | 0 | 0 | 0 | 0 | 0 | ▓ | 0 | 0 | 0 | 0 | 0 | 0 | 0 | 0 | 0 | 37.5 | 375 | 375 | 0.80 | 0.93 |

FIG. 6

Screed Pass Quality
Number Map

FIG. 7

Alert Map (Machine Attitude, X's show where alert occurs)

FIG. 8

CONCRETE SCREEDING SYSTEM WITH FLOOR QUALITY FEEDBACK/CONTROL

CROSS REFERENCE TO RELATED APPLICATIONS

The present application is a continuation of U.S. patent application Ser. No. 14/697,964, filed Apr. 28, 2015, now U.S. Pat. No. 9,835,610, which claims the filing benefits of U.S. provisional application Ser. No. 61/985,008, filed Apr. 28, 2014, which is hereby incorporated herein by reference in its entirety.

FIELD OF THE INVENTION

The present invention relates generally to an apparatus and method for improving the operation of a concrete screeding machine during the leveling and smoothing of freshly poured concrete that has been placed over a surface.

BACKGROUND OF THE INVENTION

Screeding devices or machines are used to level and smooth uncured concrete to a desired grade. Known screeding machines typically include a screed head, which includes a vibrating member and a grade setting device, such as a plow and an auger device. The screed head is vertically adjustable, such as in response to a laser leveling system, to establish the desired grade at the vibrating member. Examples of such screeding machines are described in U.S. Pat. Nos. 4,655,633; 4,930,935; 6,227,761; 7,044,681; 7,175,363 and/or 7,396,186, which are hereby incorporated herein by reference in their entireties.

The screeding machine is operable to make a number of passes over a concrete surface to screed the concrete and provide a generally flat and smooth surface. It is often desired to achieve a desired level or degree of flatness or levelness of a floor or surface, with the flatness and levelness determined after the screeding is completed and after the concrete has cured. If an error occurs during the screeding of the concrete, the desired flatness may not be achieved and the error may not be discovered until after the project is completed.

Typically, concrete floors are measured for levelness and flatness after the machine has completed the screeding process and after all of the workers have left the jobsite, long after the concrete is hardened. These levelness (FL) and flatness (FF) measurements take into account everything from job setup, laser setup, grade setup, panning, troweling, and the like, and the operators and contractor will not know how the floor measured until the project is completed and it is too late to correct. If the floor does not meet its specification, this can result in lost revenue for the concrete contractor. Furthermore, all the contractor knows is the final measurement numbers and the contractor does not get any feedback as to how any errors occurred so the contractor does not know what to change so that it does not happen again on the next floor.

SUMMARY OF THE INVENTION

The present invention provides a screeding system and floor levelness system for a screeding machine that comprises a screed head having a vibrating member and a grade setting device. The screeding or floor levelness system is operable to measure or determine or collect data pertaining to the operation of the screeding machine and the concrete being screeded to provide feedback as to the flatness and/or levelness of the surface during the screeding process. The feedback may be in the form of an alert or communication to the screeding machine operator so the operator may adjust one or more screeding parameters (such as speed of screed pass, elevation of the side regions of the screed head assembly, angle of attack or pitch or roll of the screed head assembly and/or the like) to achieve a desired or targeted flatness/levelness of the concrete surface, or the feedback may be in the form of automatic control or correction of one or more parameters of the screeding machine to achieve the desired or targeted flatness/levelness of the concrete surface.

According to an aspect of the present invention, a screeding or floor levelness system for use with a screeding machine during screeding of an uncured concrete surface includes a plurality of sensors disposed at a screeding machine having a screed head assembly that is movable over uncured concrete to screed the concrete surface. The plurality of sensors may include elevation sensors that sense an elevation of said screed head assembly relative to a reference plane established at the concrete area, and optionally may include, for example, at least one speed sensor that senses a rate of travel of the screed head assembly as it moves over the uncured concrete during a screeding pass, and/or at least one angle sensor that senses an angle of the screed head assembly as it moves over the uncured concrete during a screeding pass. A control is operable to process data captured by the sensors while the screeding machine is screeding the uncured concrete surface. Responsive to the data processing, the control estimates a flatness or levelness or quality of the surface of the concrete being screeded. While the screeding machine is screeding the uncured concrete surface, the control generates an output indicative of the estimated flatness or levelness or quality of the surface.

Optionally, the generated output comprises a display viewable by an operator of the screeding machine. The display may display at least one of (i) a value representative of an estimate of a floor quality (such as flatness or levelness) rating for the overall concrete surface, (ii) a value representative of a floor quality rating for a particular screeding pass, and (iii) an alert that the screeding pass speed is too fast or too slow. The operator, responsive to viewing the display, may adjust one or more machine parameters or controls to accommodate a determined error or flaw in the screeded surface as determined by processing of the data. Optionally, the generated output may comprise a control output that controls at least one aspect of the screeding machine to automatically accommodate a determined error or flaw in the screeded surface as determined by processing of the data.

Therefore, the present invention provides a screeding or floor levelness system that collects and processes data captured by sensors of the screeding machine, in order to provide a real time analysis and evaluation of the quality of the screeding of the concrete surface and may provide feedback during the screeding process to correct for any issues determined by the system via the data processing. For example, the system may generate an alert to the operator or may control one or more aspects of the screeding machine when the system determines that the screeding process is outside of an acceptable or targeted range or level of flatness/levelness/quality of the floor. The system of the present invention thus provides for enhanced control of the screeding machine during a screeding process to provide for enhanced quality of the screeded floors or concrete surfaces.

These and other objects, advantages, purposes and features of the present invention will become apparent upon review of the following specification in conjunction with the drawings.

BRIEF DESCRIPTION OF THE DRAWINGS

FIG. 6 is a screed pass details report generated by the system of the present invention to indicate screed pass data and statistics;

FIG. 7 is a screed pass quality number map generated by the system of the present invention to indicate the screed pass quality numbers or ratings or points for each row and pass at a job site; and FIG. 8 is an alert map generated by the system of the present invention to indicate where alerts were generated during screeding of rows and passes at the job site.

DESCRIPTION OF THE PREFERRED EMBODIMENTS

Figure 1:
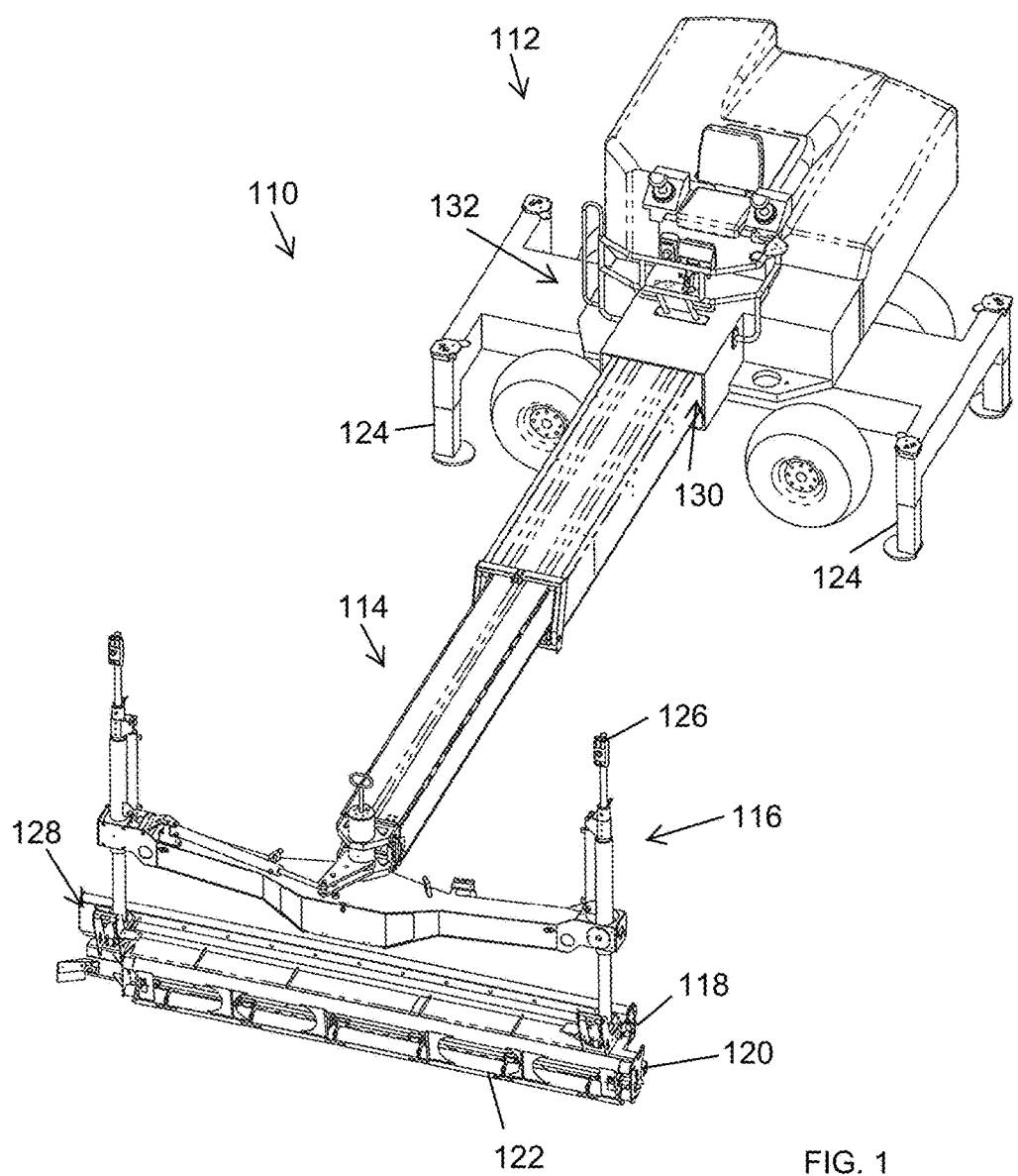
FIG. 1 is a perspective view of a concrete leveling and screeding machine that incorporates the screeding or floor levelness system of the present invention.

Referring now to the drawings and the illustrative embodiments depicted therein, a screeding machine 110 includes a wheeled unit 112 with a boom 114 extending therefrom and supporting a screeding head or assembly 116 at an outer end thereof (FIG. 1). The wheeled unit 112 is drivable to a targeted area at a support surface with uncured concrete placed thereat, and the wheeled unit may rotate about a base portion to swing the boom and screeding head to a targeted location. The boom 114 is extendable and retractable to move the screeding head 116 over the placed concrete, while the screeding head 116 is operable to establish a desired grade of the concrete surface and smooth or finish or screed the concrete. In the illustrated embodiment, the screeding head includes a plow 118, an auger 120 and a vibrating member 122 (FIG. 1). The screeding machine includes a plurality of stabilizers 124 that are extendable and retractable to support and stabilize the machine on the support surface during the screeding operation. The screeding machine 110 includes various sensors, such as laser receivers 126 at opposite ends of the screed head 116, screed head angle sensors 128 (that may sense the screed head pitch and roll), boom extension/retraction speed sensors 130, and machine levelness or attitude sensors 132, and the screeding system is operable responsive to such sensors to determine the operating level of the machine as it screeds the concrete, as discussed below.

The screeding or floor levelness system of the present invention is suitable for use on a large screeding machine 110 and the screeding head or assembly 116, which may be similar in construction and/or operation as the screeding machines and screeding heads described in U.S. Pat. Nos. 4,655,633; 4,930,935; 6,227,761; 7,044,681; 7,175,363 and/or 7,396,186, and/or U.S. Publication Nos. US-2007-0116520 and/or US-2010-0196096, which are all hereby incorporated herein by reference in their entireties, such that a detailed discussion of the overall construction and operation of the screeding machines and screeding heads need not be repeated herein. For example, the screeding machine may comprise or may utilize aspects of a Somero LASER SCREED™ screeding machine. However, clearly this example is not intended to limit the scope of the present application and clearly aspects of the present invention are suitable for use on other types of screeding machines. For example, the screeding system of the present invention may be suitable for use on smaller screeding machines, such as machines of the types described in U.S. Pat. Nos. 6,976,805; 7,121,762 and/or 7,850,396, which are hereby incorporated herein by reference in their entireties.

The present invention provides an early warning system for the screed operator so that the contractor can correct issues when they happen and before the screeding project is completed. The system of the present invention provides for constant improvement and consistency and provides data for review and analysis for post jobsite quality concerns.

The system is operable in response to various sensors at or on the screeding machine and, responsive to those sensors, the system provides an early warning indicator that something is wrong (such as during a screeding pass and/or after each screeding pass). For example, the system may calculate a current or instant FL number or FL data after each screed pass and may provide an updated jobsite average of the FL number for the floor (such as a statistical prediction of the overall floor quality (such as flatness and/or levelness) based on data collected up to that particular time). The collected data may be stored so that the data is available after the project is completed for further analysis (such as by storing as a "flight log").

The system may not necessarily calculate an FL number, but instead may calculate a pass quality number or numbers that is/are a statistical prediction of the floor quality or levelness for that screed pass. The system may display one or more pass quality numbers. For example, the pass quality numbers may be separate for left or right sides of the head or separate for different sensors that are available. Optionally, the various sensor outputs may be combined to produce a single pass quality number.

The system of the present invention thus may identify impacts of the operator's methods or actions (such as the boom speed, rotation of the screed head or of the machine, boom bounce and/or the like). The system may identify a consistent side of a control "dead band" due to machine attitude, and may identify issues related to the beginning of a screeding pass versus the end of a screed pass due to boom sag. The system may identify laser reflections and interference (between one or both of the laser receivers and the laser plane emitting device that emits a laser plane at the worksite). The system may identify grade changes that may occur after column block occurs—such as when entering a column block situation versus when exiting the column block situation. The system may also identify issues related to poor touchdowns or landings of the screed head at the beginning of passes, and may identify if the left or right elevation valve speeds (that control the vertical adjustment or speed of the sides of the screed head in response to the operator and/or the laser receivers) are too fast or too slow.

The screed position at a jobsite is not known, and there is no direct correlation of FL numbers vs. screed position. The system of the present invention may time stamp collected data and time stamp when passes occur to have the pass data time stamped to at least estimate the screed head location or position at the jobsite. The system may also provide the ability to log the row or pass number with the data. The row number may be manually incremented by the operator or automatically incremented based on machine motion. This will help to track the screed pass data to a physical location at the jobsite, which makes it easier to correlate screed data to the physical location.

By correlating the data with the time or location, the system may analyze the data to determine what happened at or near any given location at the jobsite to determine what error may have occurred at a location where there may be an imperfection or flaw in the finished concrete surface or floor. Thus, the system of the present invention may provide post job analyses/reports that may show the screed quality numbers or floor quality numbers for each pass and at any given location and for the entire screeding job or project (with the numbers processed being attributable to particular locations or passes via the time stamping of data or via other suitable parameters or identifiers).

Thus, the system of the present invention may collect data captured by various sensors at the screeding machine and/or at the jobsite. The system may, while the screeding machine is screeding the concrete, process captured and collected data to determine an estimate as to the floor flatness or floor levelness or floor quality. Responsive to such data processing, the system may provide feedback to the operator so that the operator may adjust one or more machine settings or operation parameters to accommodate any errors or flaws determined by the system. Optionally, responsive to such data processing, the system may automatically adjust one or more machine settings and/or operation parameters to automatically accommodate and correct for any errors or flaws determined by the system.

Figure 2:
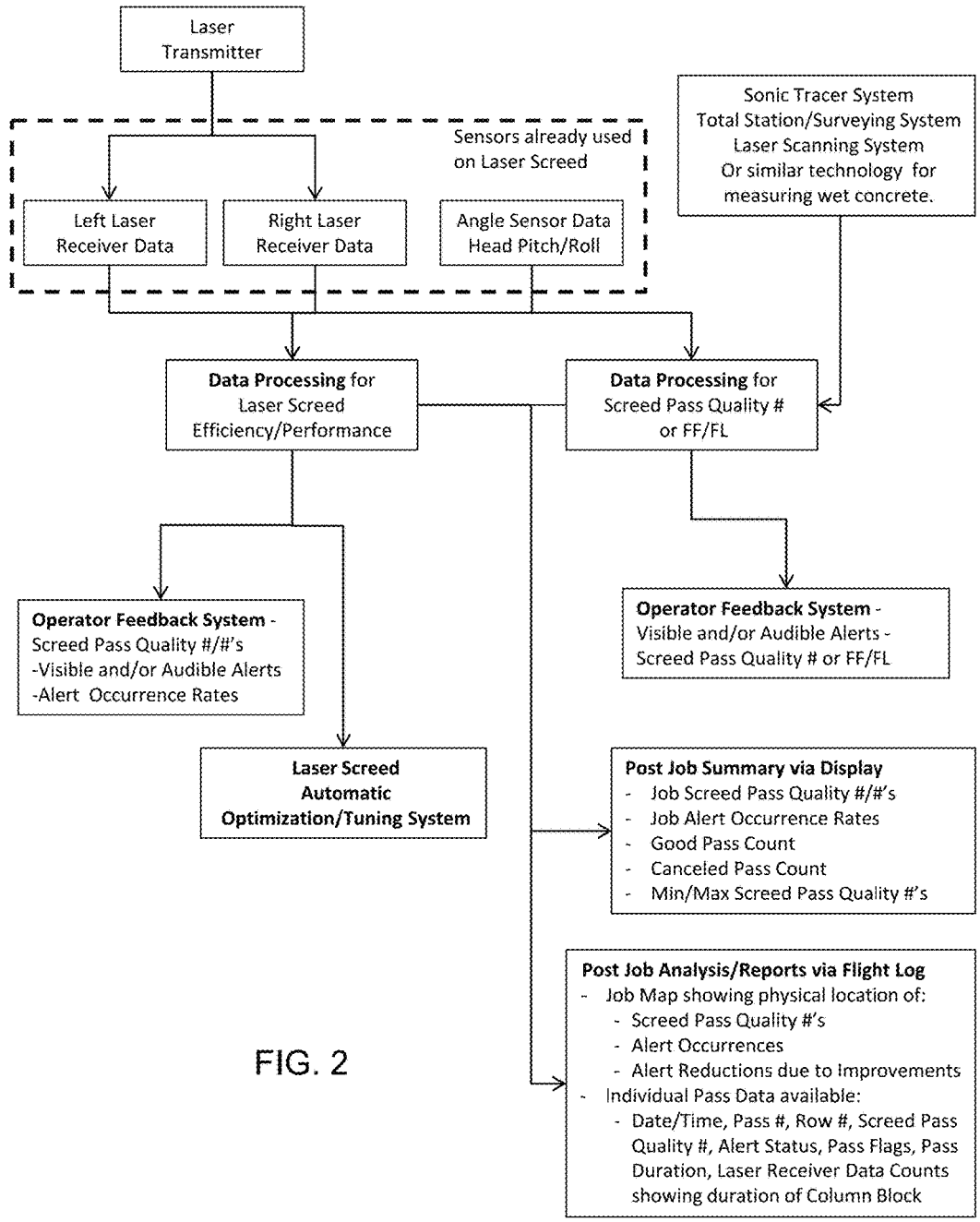
FIG. 2 is a flowchart showing the system or process of the present invention.

Thus, and as can be seen with reference to FIG. 2, the system of the present invention is operable to collect or capture data via sensors already in use on the screeding machine, such as left and right laser receivers at the screed head and screed head angle sensor data (that captures data indicative of the screed head pitch and roll). The data is processed to determine the laser screeding efficiency and performance and/or the floor quality or levelness or flatness (and may determine a real time estimate of floor quality or levelness or flatness during the screeding process). Responsive to the data processing, the system may provide operator feedback, such as visible and/or audible alerts (such as when the system determines that the screeding machine is not meeting a desired quality or levelness or flatness of the floor) and/or may provide a real time estimate of the screeding quality or floor quality so the operator can readily determine if he or she is operating the screeding machine within the appropriate parameters to achieve the targeted quality or levelness or flatness. Optionally, the data processing may also be responsive to a sonic tracer system or total station/surveying system or laser scanning system that may measure or analyze or evaluate the surface of wet uncured concrete.

Figure 4:
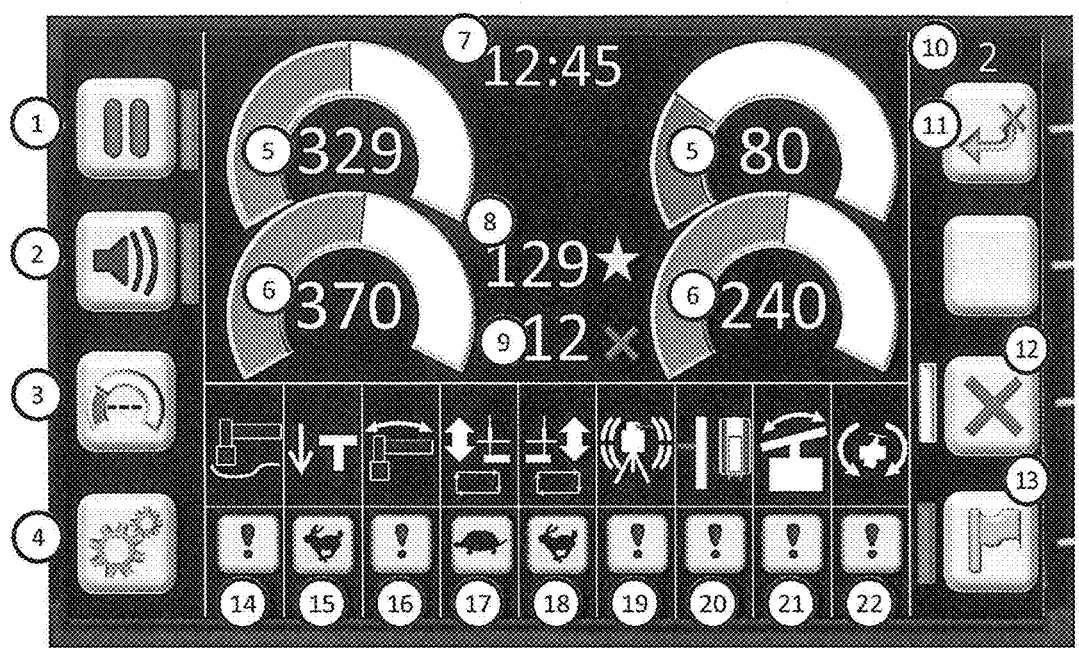
FIG. 4 is a view of an operator feedback screen for use with the screeding or floor levelness system of the present invention.
Figure 5:
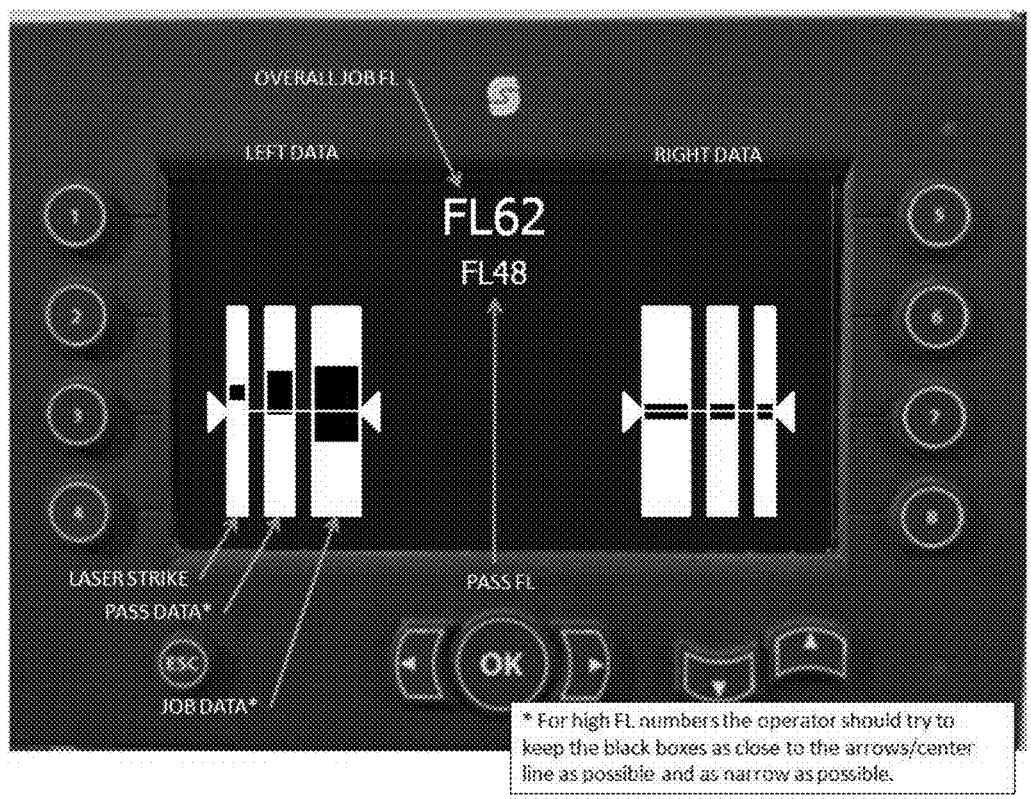
FIG. 5 is a view of another operator feedback screen for use with the screeding or floor levelness system of the present invention.

For example, and as shown in FIG. 4, the system may provide a display that is viewable by the operator, with the display providing information pertaining to how the operator is doing for each pass and for the overall job. In the illustrated embodiment, the display provides pass information and overall job information in the form of a screed pass quality number, where the operator may adjust the operating parameters (such as pass speed, left/right vertical adjustment, pitch/roll of the screed head, levelness of the machine and/or the like) to try to increase the screed pass quality number (representative of the screeding performance), so the operator can determine and respond when a particular pass is at a lower quality or levelness or flatness degree or level or amount as compared to other passes and/or the overall job. Optionally, and such as can be seen with reference to FIG. 5, the display may provide pass information and/or overall job information in the form of sliding scales, where the operator may adjust the operating parameters to keep the sliding scales or pointers within a desired or marked range on the display screen.

In the illustrated embodiment of FIG. 4, the display screen displays information for viewing by the operator during each screed pass of the screeding process at a particular jobsite. The display screen may comprise a touch screen so that the driver may touch different user input regions to actuate or adjust various controls or features of the screeding system. The display displays information pertaining to the screed pass quality and may provide various visual alerts or indications to the operator during the screeding process.

For example, and as shown in FIG. 4, the display screen may include a record/pause button 1, a sound on/off button 2 (which turns on or off an audible alert that may alert the operator of low pass quality numbers or the like), a pass quality alert level 3 (which allows the operator to set a desired alert warning level depending on the particular operator) and a setup menu access 4. The principal display area may display indications of the screed quality, and may adjust the display indications (such as adjust the appearance and/or color of the indications) depending on the determined quality of the screed pass. For example, the principal display area may display a left/right pass quality number and gauge 5, a left/right overall job average screed pass quality number and gauge 6, a real time clock 7 (optionally a user selectable 12 or 24 hour format), a good pass count 8 and a canceled pass count 9 (the operator can cancel a bad pass because the operator may choose to re-screed that pass—a canceled pass does not get included in the jobsite screed pass quality or the alert percentage reporting).

The display screen may also disclose a row count 10, an increment row button 11 (for manually incrementing the row number or count during a screeding process), a cancel pass button 12 and a flag button 13 (the operator can flag a pass to manually mark an event that occurred during the screed pass, and can select multiple flags to track different events. The display screen may also display various alerts or indicators, such as, for example, a poor touchdown alert 14, a boom speed too fast or slow alert 15 (with, for example, a rabbit showing when it is too fast and a turtle showing when it is too slow), a machine attitude incorrect alert 16, a left valve speed too fast or slow alert 17 (with a rabbit showing when it is too fast and a turtle showing when it is too slow), a right valve speed too fast or slow alert 18 (with a rabbit showing when it is too fast and a turtle showing when it is too slow). Also, or otherwise, the display screen may display a poor laser quality or vibration alert 19, a column block alert 20, a head rotate alert 21 and a machine rotate alert 22. For the alerts, the display screen may change the color (such as, for example, turn on a yellow indicator or the like) or flash the visual alerts, and may adjust the color or rate of flash responsive to a degree of problem or issue associated with the alert. For example, the display screen may initially show an alert icon as yellow, but may change that icon to red if the problem persists or worsens.

Figure 3:
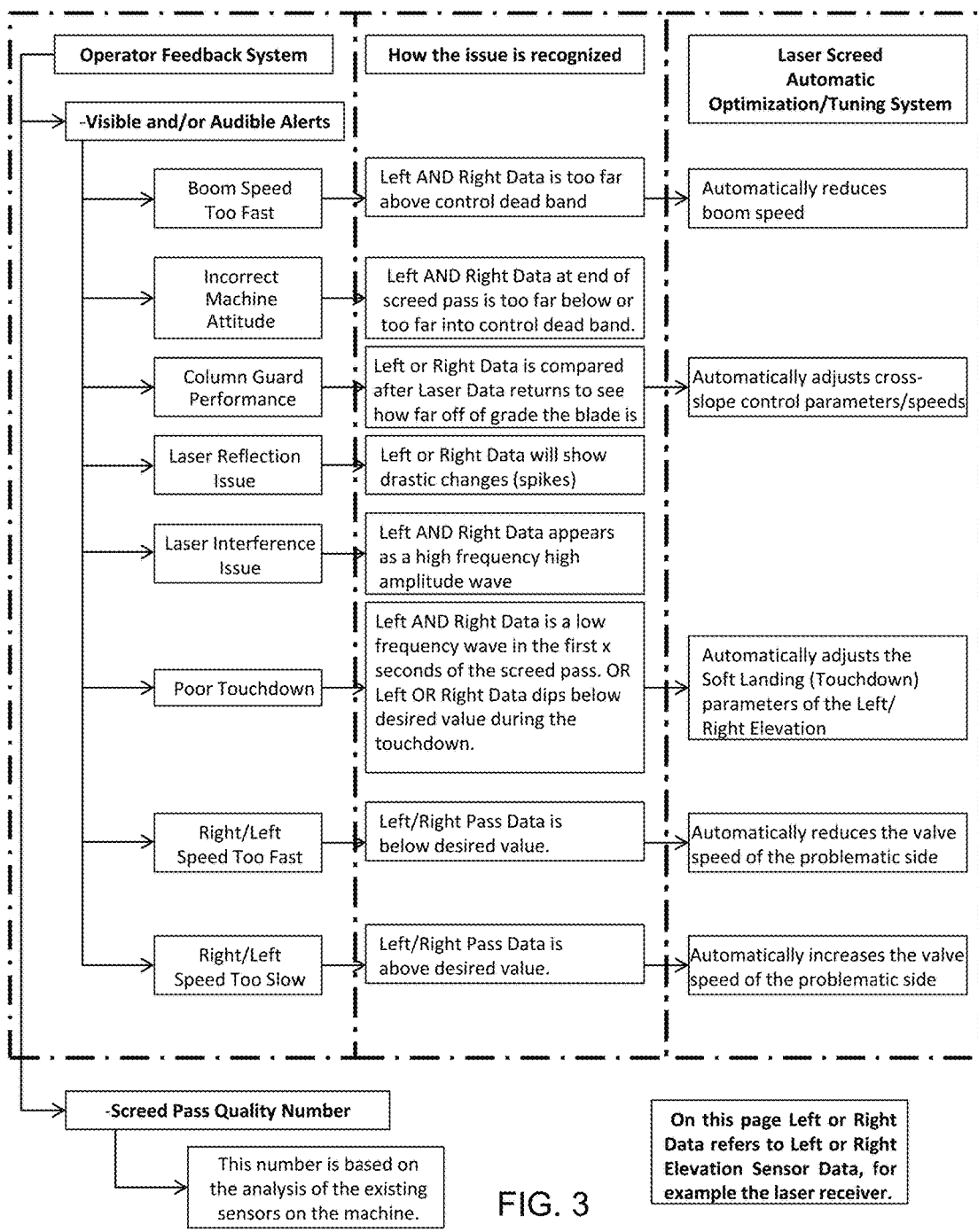
FIG. 3 is a flowchart showing aspects of the operator feedback system and automatic adjusting system of the screeding or floor levelness system of the present invention.

Thus, and as shown in FIG. 3, the operator feedback system may provide various alerts or information to the operator during the screeding process. The operator may thus be informed as to (i) when the boom speed is too fast or slow for any given pass, (ii) when the machine is not level or at an incorrect attitude, (iii) when there is a column block issue or column guard performance issue, (iv) when there is a laser reflection issue or laser interference issue, (v) when there is a poor touchdown or landing of the screed head at the concrete surface, (vi) when the left or right vertical actuators or valve speeds are too fast or too slow. For example, the operator may receive a "poor touchdown" alert or a "machine attitude incorrect" alert or a "boom speed too fast" alert or a "boom speed too slow" alert or a "left elevation valve speed too fast" alert or a "left elevation valve speed too slow" alert or a "right elevation valve speed too fast" alert or a "right elevation valve speed too slow" alert or "laser reflection/interference" alert or the like, depending on the issue determined by the system in response to the data processing. The operator may readily adjust one or more of the operating parameters in response to such alerts. Note the "left/right data" indications shown in FIG. 3 refer to left or right elevation sensor data, such as data collected from the laser receiver indicative of where the laser plane is detected by the laser receiver during the screeding operation.

Optionally, the system of the present invention may automatically control one or more machine parameters in response to the data processing. For example, and as also shown in FIG. 3, the system may automatically reduce the boom speed or may automatically adjust the cross-slope control parameters or speeds or may automatically adjust the soft landing parameters of the left/right elevation cylinders/controls or may automatically increase or decrease the valve speeds, depending on the particular issue determined by the system via the data processing.

The system of the present invention thus collects and processes data from multiple sensors of the screeding machine to determine the performance of the operator and screeding machine during the screeding process. For example, the system may read and/or store the existing screed sensors (such as left and right elevation data and angle sensor data) and/or other technology capable of measuring wet (uncured/partially cured) concrete. The system evaluates this data to calculate a statistical prediction of the screed pass flatness (and may approximate the FL number or rating or may provide any suitable rating number). For example, the system's statistical prediction may be based on the ASTM E-1155-96 standard for calculating an actual FL number for a finished/hardened concrete floor. The formula may be modified to apply to the particular screeding machine. Because the screeding machine may only measure one pass at a time instead of many passes (as required by ASTM E-1155-96), the formula preferably also contains a job data average so that the individual passes can be compared to the overall job for consistency. The system thus may combine the individual screed passes into an overall job (composite) flatness estimation or approximated FL number or job screed pass quality number.

The system of the present invention thus provides a screed pass quality number, which may be calculated responsive to inputs from various sensors or devices of the screeding machine. The system may calculate the screed pass quality number independently for the right and left sides. The calculation may be done based solely or substantially on laser receiver data. The calculation is live, so that the system provides feedback in real time. For example, the calculation may define the greatest possible result as 500 (excellent) and the lowest possible result as zero (poor). The calculation may be a point-based system that awards the operator with points for maintaining grade and deducts points for high or low spots that occurred during the screed pass or passes.

For example, the system may collect laser receiver data in an array during a screed pass, and every consecutive set of data points may be analyzed. The size of the set of data points may be selected to represent a measurement roughly every foot of screed head travel to more closely approximate an FL measurement. From this data, the errors are calculated by determining how far the data resides from the desired value.

The errors are then used to award points for being close to the target value or deduct points for being far from the target value. The point scale and level are configurable to determine a desirable point system to accurately report floor or surface quality. The point system may have one of more levels for points awarded and/or points deducted.

Such a process may be repeated for each set of data points. The points are combined by averaging points awarded (so the maximum points earned is 500), but deducted points are cumulative. Thus, as the system detects defects in the floor, those defects will remain reported and cannot be diminished due to awarded points in other passes. As the quantity or magnitude of the defects increase, the overall score will continue to decrease.

At the end of the screed pass, the system reports the overall screed pass quality number. If the operator does nothing, the pass will be recorded towards the overall job total. If the operator cancels the pass, the operator has the opportunity to re-screed the pass and the overall job total is not affected. The overall job total may be calculated as an average of each individual pass quality number.

Thus, the present invention provides a system that collects and processes data from multiple sensors of the screeding machine (such as speed sensors sensing the rate of extension and retraction of the boom, elevation sensors sensing the elevation of the screed head relative to a targeted or desired elevation or plane, speed sensors sensing the rate of adjustment of the screed head, angle sensors sensing the pitch or roll or angle of attack of the screed head, sensors sensing the levelness or attitude of the screeding machine and/or the like). Responsive to such processing, the system determines how the machine/operator is performing during any given screed pass and/or during the overall project (involving multiple screed passes). The system may then generate one or more alerts or warnings or messages to the operator so the operator may adjust one or more machine parameters or controls to adjust the screeding process to address or correct any errors or flaws or inconsistencies determined by the system during the previous screed passes or current screed pass. Optionally, responsive to a determination of an error or deviation from the targeted flatness or levelness or quality level, the system may automatically adjust or control one or more aspects of the screeding machine to correct for such errors or deviations so that the floor being processed is within the targeted flatness or levelness or quality levels. The automatic control may override the operator's controls or may be overridden by the operator, depending on the particular application of the screeding system and screeding machine of the present invention.

The operator may start the process by pressing a "record" button or key or input, and then may begin screeding the job site. Because the recording is activated, the system will automatically record screed pass data for all of the screed passes. The operator may pause the recording if desired, whereby the screed data being collected will not be recorded (and the overall job data and pass counts will not be updated) until the recording feature is activated. During the screeding process, the system generates an alert to the operator if one or more aspects of the screeding process are determined to be performed incorrectly or not optimally. For example, the system may generate (i) a poor touchdown alert if the screed head dips too far into the concrete at the onset of the screeding pass, or (ii) the system may generate a boom speed to fast alert if the screed head is determined to be traveling too fast to accurately hold the grade (whereby the operator may adjust the speed accordingly), or (iii) a machine attitude (stabilizer) incorrect alert if the system determines that the machine is pitched forward or backward, or (iv) a head or machine rotate alert that detects and warns when a head rotate function (that allows the screed head to maneuver around columns and obstacles) or a machine rotate function (that also or otherwise allows the screed head to maneuver around columns and obstacles) is used, or (v) a left/right valve speed too fast alert if the screed head is moving at a speed that may cause the grade to be cut lower than desired, or (vi) a left/right valve speed too slow alert if the screed head is moving at a speed that may leave high spots in the floor, or (vii) a poor laser quality/vibration alert if laser vibration occurs that can cause the screed head to oscillate a threshold amount, or (viii) a column block alert if the system determines that a laser receiver is blocked from the laser plane/beam by a column or obstacle.

Figures 7, 8:
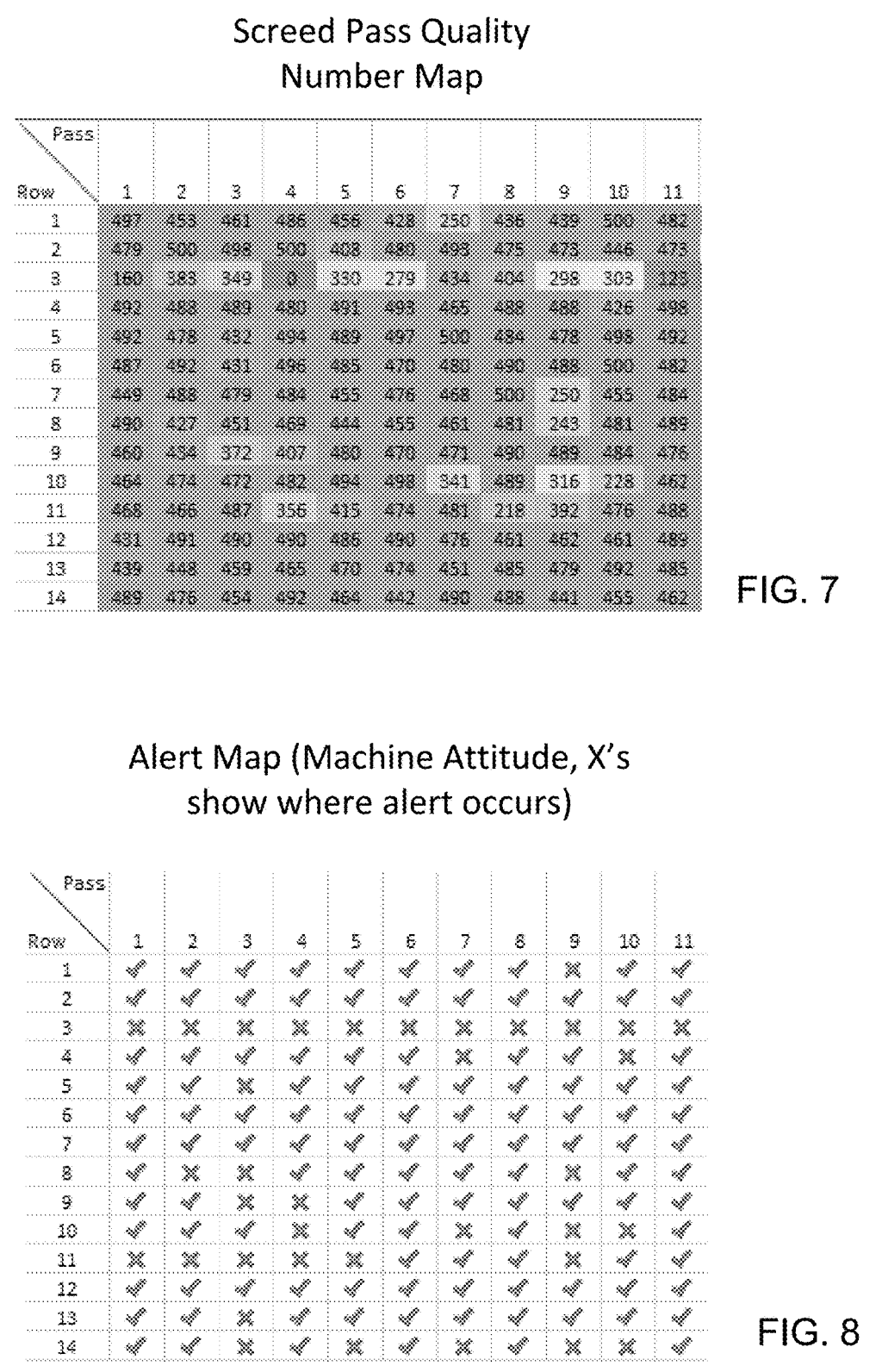

The system thus provides alerts for various issues that may occur during the screeding process. Additionally, the system of the present invention provides a reporting feature that provides screed pass details (FIG. 6) that shows summary information for the screed passes, such as where flags or alerts were set and the screed pass statistics (pass duration, data counts, data averages). The reporting feature may also or otherwise provide a screed pass quality number map (FIG. 7) that shows the screed pass quality number value for each pass/row, so the operator can review which rows were better or worse than others. The reporting feature may also or otherwise provide an alert map (FIG. 8) that shows where alerts were generated during the screeding process. Thus, the reports provide summaries of the screeding process for the job site so that the operator, when reviewing the reports can determine where the difficulties/problems occurred. The reports or flight logs may be color coded (such as a "heat map" showing dark green for very good passes/rows, and light green, yellow, orange and red for progressively poorer passes/rows) so that the operator, with just a quick glance at the reports, can see how the job is going and can determine where he or she is struggling or having difficulties.

Optionally, the screed pass data can be exported from the system and machine to a USB memory stick or the like, so that the data can be later transferred to a computer for saving and/or for further processing. Optionally, the screed pass data may be wirelessly communicated to a computer or server or device for saving and/or for further processing.

Therefore, the present invention provides a system that, by utilizing sensors that are typically already on the screeding machine, may provide feedback and enhanced control of the machine to achieve desired or targeted flatness or levelness or quality levels of the screeded floor. The system provides such feedback and/or control during the screeding process so that any issues determined during the screeding process may be corrected before the job is completed, thus resulting in improved floor quality. Thus, the system of the present invention provides accelerated learning by the operator during (not after) the screeding process. The system removes variables in operators by providing real time feedback to the operator so the operator can adjust or control the machine accordingly.

Changes and modifications to the specifically described embodiments can be carried out without departing from the principles of the present invention, which is intended to be limited only by the scope of the appended claims as interpreted according to the principles of patent law.

The invention claimed is:

1. A method for screeding an uncured concrete surface using a screeding machine, said method comprising:
   providing a screeding machine having a plurality of sensors and a screed head assembly, wherein the sensors include elevation sensors that sense an elevation of the screed head assembly relative to a reference plane established at the concrete area;
   providing a control;
   screeding the uncured concrete surface via the screeding machine moving the screed head assembly at the uncured concrete surface;
   processing, via the control, data captured by the sensors while the screeding machine is screeding the uncured concrete surface;
   determining at least one screeding aspect via processing, via the control, data captured by the sensors while the screeding machine is screeding the uncured concrete surface;
   wherein determining at least one screeding aspect comprises determining (i) a rate of movement of the screed head assembly while the screeding machine is screeding the uncured concrete surface, (ii) a machine attitude of the screeding machine and/or screed head assembly while the screeding machine is screeding the uncured concrete surface, (iii) pitch of the screed head assembly while the screeding machine is screeding the uncured concrete surface, and/or (iv) roll of the screed head assembly while the screeding machine is screeding the uncured concrete surface;
   while the screeding machine is screeding the uncured concrete surface, and responsive to data processing by the control of data captured by the sensors while the screeding machine is screeding the uncured concrete surface, estimating, via the control, a flatness or levelness or quality of the surface of the concrete surface being screeded; and
   generating, via the control, and while the screeding machine is screeding the uncured concrete surface, an output indicative of the estimated flatness or levelness or quality of the surface.

2. The method of claim 1, comprising displaying, responsive to the output, information at a display that viewable by an operator of the screeding machine while the screeding machine is screeding the uncured concrete surface.

3. The method of claim 2, wherein displaying information comprises displaying a value representative of an estimate of a floor quality rating for the concrete surface.

4. The method of claim 2, wherein displaying information comprises displaying a value representative of a floor quality rating for a particular screeding pass.

5. The method of claim 1, comprising controlling at least one aspect of the screeding machine responsive to the output.

6. The method of claim 1, comprising adjusting control of the screeding machine responsive to the output.

7. The method of claim 1, comprising collecting data captured by the sensors and processing the captured data after completion of screeding of the concrete area by the screeding machine.

8. The method of claim 7, comprising (i) time stamping data captured by the sensors while the screeding machine is screeding the uncured concrete surface, and (ii) correlating the time stamps with the location of the screed head assembly as the screeding machine screeds the uncured concrete surface.

9. The method of claim 7, comprising tracking, via the control, data for particular screeding passes.

10. The method of claim 1, wherein the screed head assembly is movable via an extendable and retractable boom of the screeding machine, and wherein said method comprises determining, responsive to data processing of data captured by the plurality of sensors, a rate of extension or retraction of the boom during a screeding pass and while the screeding machine is screeding the uncured concrete surface.

11. The method of claim 10, wherein the plurality of sensors comprises at least one attitude sensor that senses an attitude of the boom, and wherein said method comprises, responsive to determination, via processing of data captured by the at least one attitude sensor, that the attitude of the boom is above an upper threshold level or below a lower threshold level, generating, via the control, an alert to an operator of the screeding machine while the screeding machine is screeding the uncured concrete surface.

12. The method of claim 1, wherein determining at least one screed aspect comprises determining when at least one screed aspect is above or below a threshold level.

13. The method of claim 12, wherein determining at least one screeding aspect comprises determining a rate of movement of the screed head assembly while the screeding machine is screeding the uncured concrete surface, and wherein said method comprises, responsive to determination of the rate of movement being above an upper threshold level or below a lower threshold level, generating, via the control, an alert to an operator of the screeding machine while the screeding machine is screeding the uncured concrete surface.

14. The method of claim 12, wherein determining at least one screeding aspect comprises determining a machine attitude of the screeding machine and/or screed head assembly while the screeding machine is screeding the uncured concrete surface, and wherein said method comprises, responsive to determination of the machine attitude being above an upper threshold level or below a lower threshold level, generating, via the control, an alert to an operator of the screeding machine while the screeding machine is screeding the uncured concrete surface.

15. The method of claim 12, wherein determining at least one screeding aspect comprises determining pitch or yaw of the screed head assembly while the screeding machine is screeding the uncured concrete surface, and wherein said method comprises, responsive to determination of the pitch or yaw being above an upper threshold level or below a lower threshold level, generating, via the control, an alert to an operator of the screeding machine while the screeding machine is screeding the uncured concrete surface.

16. The method of claim 12, wherein determining when at least one screed aspect is above or below a threshold level comprises determining when (i) a screed head touchdown is more than a threshold amount into the concrete, (ii) laser reflections or vibrations or interference are above a threshold level, (iii) screeding machine rotation is beyond a threshold level and/or (iv) screed head assembly rotation is beyond a threshold level.

17. The method of claim 1, comprising, upon completion of a screed pass or completion of screeding a job site, reporting (i) screed pass details for the screed passes at the job site, (ii) screed pass statistics for the screed passes at the job site, (iii) screed pass quality values or points for the screed passes at the job site and/or (iv) an alert map showing where alerts were generated for the screed passes at the job site.

18. A method for screeding an uncured concrete surface using a screeding machine, said method comprising:
providing a screeding machine having a plurality of sensors and a screed head assembly, wherein the sensors include elevation sensors that sense an elevation of the screed head assembly relative to a reference plane established at the concrete area;
providing a control;
screeding the uncured concrete surface via the screeding machine moving the screed head assembly at the uncured concrete surface;
processing, via the control, data captured by the sensors while the screeding machine is screeding the uncured concrete surface;
while the screeding machine is screeding the uncured concrete surface, and responsive to data processing by the control of data captured by the sensors while the screeding machine is screeding the uncured concrete surface, estimating, via the control, a flatness or levelness or quality of the surface of the concrete surface being screeded; and
displaying information at a display that viewable by an operator of the screeding machine while the screeding machine is screeding the uncured concrete surface, wherein the displayed information is associated with the estimated flatness or levelness or quality of the surface.

19. The method of claim 18, wherein displaying information comprises displaying a value representative of an estimate of a floor quality rating for the concrete surface.

20. The method of claim 18, wherein displaying information comprises displaying a value representative of a floor quality rating for a particular screeding pass.

21. The method of claim 18, wherein displaying information comprises displaying an indicator of current operating parameters of the screeding machine so that the operator viewing the display can adjust the operation of the screeding machine to maintain the screeding machine performance within indicated levels of the operating parameters.

22. The method of claim 18, comprising determining, via processing of data captured by said plurality of sensors, a rate of movement of the screed head assembly while the screeding machine is screeding the uncured concrete surface, and wherein said method comprises, responsive to determination of the rate of movement being above an upper threshold level or below a lower threshold level, displaying an alert to the operator of the screeding machine while the screeding machine is screeding the uncured concrete surface.

23. The method of claim 18, comprising determining, via processing of data captured by said plurality of sensors, an attitude of the screed head assembly while the screeding machine is screeding the uncured concrete surface, and wherein said method comprises, responsive to determination of the attitude of the screed head assembly being above an upper threshold level or below a lower threshold level, displaying an alert to the operator of the screeding machine while the screeding machine is screeding the uncured concrete surface.

24. The method of claim 18, comprising determining at least one screed aspect while the screeding machine is screeding the uncured concrete surface and determining when at least one screed aspect is above or below a threshold level.

25. The method of claim 24, comprising displaying at the display, while the screeding machine is screeding the uncured concrete surface, information pertaining to the determined at least one screed aspect being above or below the threshold level.

26. The method of claim 25, wherein determining when at least one screed aspect is above or below a threshold level comprises determining when (i) a screed head touchdown is more than a threshold amount into the concrete, (ii) laser reflections or vibrations or interference are above a threshold level, (iii) screeding machine rotation is beyond a threshold level and/or (iv) screed head assembly rotation is beyond a threshold level.

27. The method of claim 18, comprising, upon completion of a screed pass or completion of screeding a job site, reporting (i) screed pass details for the screed passes at the job site, (ii) screed pass statistics for the screed passes at the job site, (iii) screed pass quality values or points for the screed passes at the job site and/or (iv) an alert map showing where alerts were generated for the screed passes at the job site.

\* \* \* \* \*